US012663395B2

(12) United States Patent (10) Patent No.: US 12,663,395 B2
Hayashi (45) Date of Patent: Jun. 23, 2026

(54) SENSOR AND SENSOR SYSTEM

(71) Applicant: KABUSHIKI KAISHA TOSHIBA, Tokyo (JP)

(72) Inventor: Yumi Hayashi, Ayase Kanagawa (JP)

(73) Assignee: KABUSHIKI KAISHA TOSHIBA, Kawasaki (JP)

( * ) Notice: Subject to any disclaimer, the term of this patent is extended or adjusted under 35 U.S.C. 154(b) by 360 days.

(21) Appl. No.: 18/365,433

(22) Filed: Aug. 4, 2023

(65) Prior Publication Data

US 2024/0201119 A1 Jun. 20, 2024

(30) Foreign Application Priority Data

Dec. 14, 2022 (JP) ................................. 2022-199719

(51) Int. Cl.
   *G01N 27/22* (2006.01)
   *G01N 33/00* (2006.01)
(52) U.S. Cl.
   CPC ......... *G01N 27/226* (2013.01); *G01N 33/005* (2013.01); *G01N 27/227* (2013.01)
(58) Field of Classification Search
   CPC ... G01N 27/226; G01N 33/005; G01N 27/227
   USPC ......................................................... 73/23.2
   See application file for complete search history.

(56) References Cited

U.S. PATENT DOCUMENTS 3,567,383 A * 3/1971 Langley ................. G01N 27/12
                                                          324/717
2010/0108529 A1 * 5/2010 Zamborini ........... G01N 33/005
                                                          205/205
2017/0131227 A1 * 5/2017 Homma .............. H01M 8/0444
2017/0343522 A1 11/2017 Ikehashi et al.
2019/0086377 A1 3/2019 Ikehashi et al.
2020/0400604 A1 * 12/2020 Jung .................... G01N 27/227
                     (Continued)

FOREIGN PATENT DOCUMENTS

JP        2017-215170 A     12/2017
JP        2019-56607 A      4/2019
                     (Continued)

OTHER PUBLICATIONS

Takahisa Tanaka et al., "Nanoscale Pt thin film sensor for accurate detection of ppm level hydrogen in air at high humidity," Sensors and Actuators: B. Chem., vol. 258, pp. 913-919 (2018).
                     (Continued)

*Primary Examiner* — Peter J Macchiarolo
*Assistant Examiner* — John M Royston
(74) *Attorney, Agent, or Firm* — Finnegan, Henderson, Farabow, Garrett & Dunner, LLP

(57) ABSTRACT

According to one embodiment, a sensor includes a base, a base including a first region and a second region, a fixed electrode fixed to the first region, a first fixed portion fixed to the second region, a first support portion, and a movable portion. The first support portion is connected to the first fixed portion. The first support portion includes a first support layer and a first layer fixed to the first support layer. The first layer includes at least one metal selected from the group consisting of Pt, Pd and Ti, and oxygen. The movable portion is supported by the first support portion. A first gap is provided between the fixed electrode and the movable portion.

19 Claims, 4 Drawing Sheets

(56)  References Cited

U.S. PATENT DOCUMENTS

| | | |
|---|---|---|
| 2021/0318282 A1 | 10/2021 | Akimoto et al. |
| 2022/0011254 A1 | 1/2022 | Hayashi |
| 2022/0018820 A1 | 1/2022 | Hiramatsu et al. |
| 2022/0082522 A1 | 3/2022 | Yamazaki |
| 2022/0276192 A1 | 9/2022 | Akimoto et al. |

FOREIGN PATENT DOCUMENTS

| | | |
|---|---|---|
| JP | 2021-167766 A | 10/2021 |
| JP | 2022-19147 A | 1/2022 |
| JP | 2022-22828 A | 2/2022 |
| JP | 2022-131000 A | 9/2022 |
| KR | 101 550 173 B1 | 9/2015 |

OTHER PUBLICATIONS

Zhicheng Cai et al., "Synthesis of Pd nanoparticle-decorated $SnO_2$ nanowires and determination of the optimum quantity of Pd nanoparticles for highly sensitive and selective hydrogen gas sensor," ScienceDirect; Sensors & Actuators: B. Chem., vol. 322, Art. 128651, 14 pages (2020).
Japan Patent Office, Office Action in JP App No. 2022-199719 (Dec. 12, 2025).

* cited by examiner

SENSOR AND SENSOR SYSTEM

CROSS-REFERENCE TO RELATED APPLICATIONS

This application is based upon and claims the benefit of priority from Japanese Patent Application No. 2022-199719, filed on Dec. 14, 2022; the entire contents of which are incorporated herein by reference.

FIELD

Embodiments described herein relate generally to a sensor and a sensor system.

BACKGROUND

For example, there are sensors that apply MEMS structures. High detection sensitivity is desired in the sensor.

DETAILED DESCRIPTION

Figure 1:
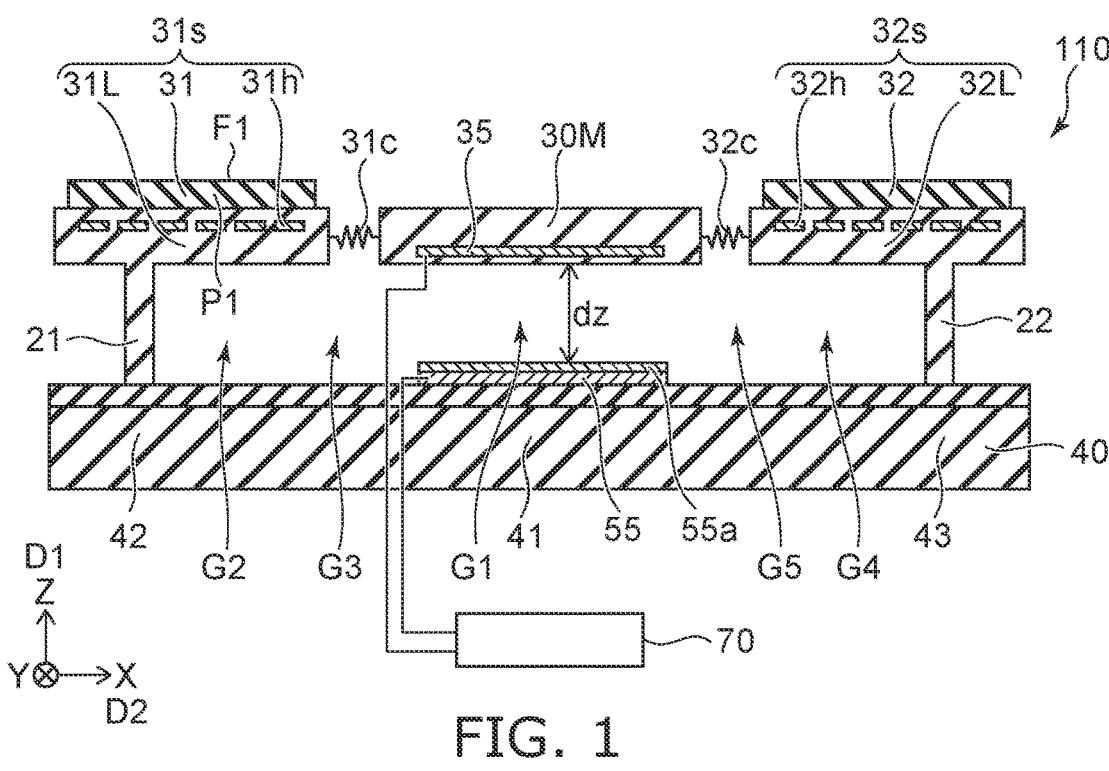
FIG. 1 is a schematic cross-sectional view illustrating a sensor according to a first embodiment.

According to one embodiment, a sensor includes a base, a base including a first region and a second region, a fixed electrode fixed to the first region, a first fixed portion fixed to the second region, a first support portion, and a movable portion. The first support portion is connected to the first fixed portion. The first support portion includes a first support layer and a first layer fixed to the first support layer. The first layer includes at least one metal selected from the group consisting of Pt, Pd and Ti, and oxygen. The movable portion is supported by the first support portion. A first gap is provided between the fixed electrode and the movable portion.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic cross-sectional view illustrating a sensor according to a first embodiment.

As shown in FIG. 1, a sensor 110 according to the embodiment includes a base 40, a fixed electrode 55, a first fixed portion 21, a first support portion 31s and a movable portion 30M.

The base 40 includes a first region 41 and a second region 42. The base 40 may be, for example, a silicon substrate.

The fixed electrode 55 is fixed to the first region 41. An insulating film 55a may be provided on the fixed electrode 55.

The first fixed portion 21 is fixed to the second region 42. The first support portion 31s is connected to the first fixed portion 21. The first support portion 31s includes a first support layer 31L and a first layer 31. The first layer 31 is fixed to the first support layer 31L.

The first layer 31 includes oxygen and at least one metal selected from the group consisting of Pt, Pd and Ti. For example, the first layer 31 includes oxides of the above metals. The first layer 31 includes bonds between the above metals and oxygen.

The movable portion 30M is supported by the first support portion 31s. A first gap G1 is provided between the fixed electrode 55 and the movable portion 30M.

For example, the first layer 31 is reduced by a detection target gas around the first layer 31. The detection target gas includes, for example, hydrogen. When the first layer 31 is reduced, for example, oxygen included in the first layer 31 is released from the first layer 31. The structure of the first layer 31 changes. For example, the volume of the first layer 31 changes.

Due to the change in the structure of the first layer 31, stress is generated between the first layer 31 and the first support layer 31L. The stress is, for example, tensile stress. For example, the first layer 31 tends to shrink with the first support layer 31L as a reference. Thereby, the shape of the first support portion 31s changes. Due to the change in the shape, the distance between the movable portion 30M and the fixed electrode 55 changes. The electrical capacitance changes as the distance changes. The detection target can be detected by detecting a change in electrical capacitance. According to the embodiments, it is possible to provide a sensor with high detection sensitivity.

As shown in FIG. 1, the movable portion 30M may include a movable electrode 35. The electrical capacitance may be the electrical capacitance between the fixed electrode 55 and the movable electrode 35.

Figure 2:
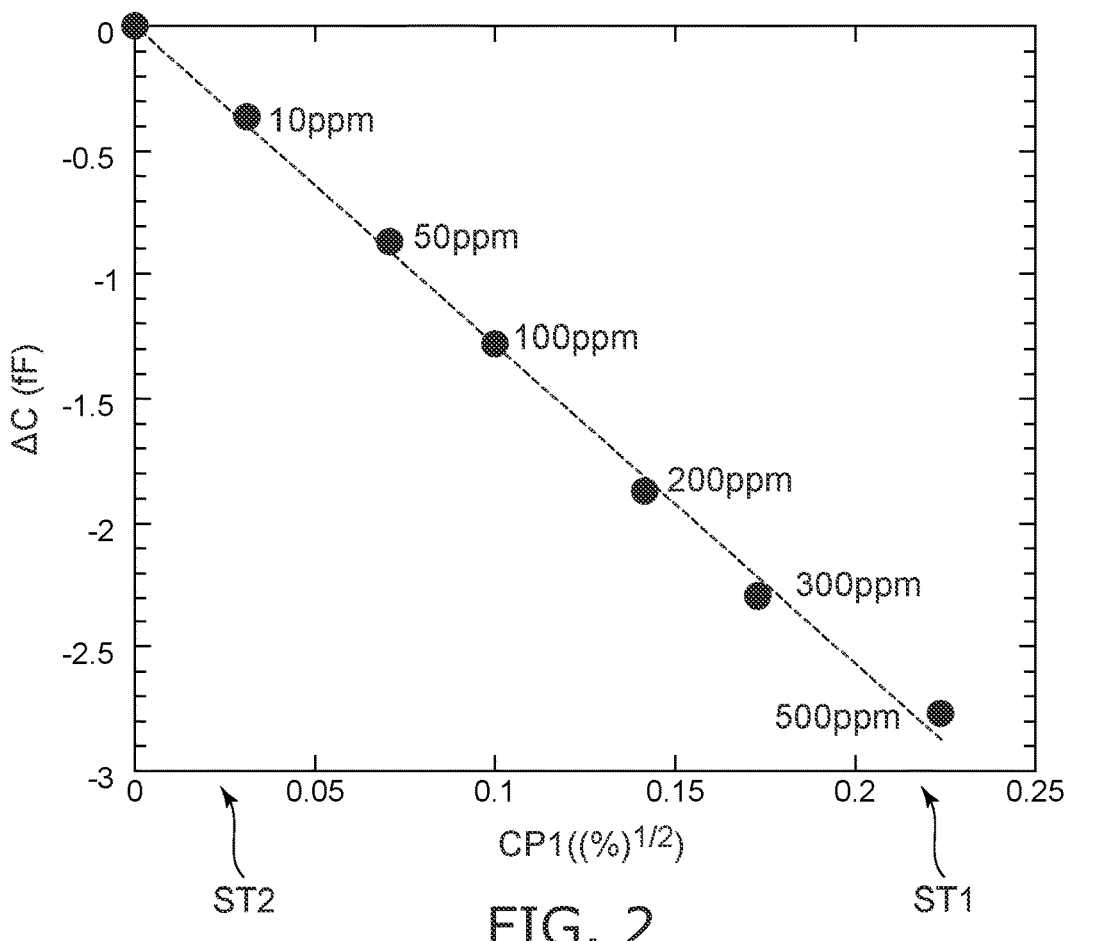
FIG. 2 is a graph illustrating characteristics of the sensor according to the first embodiment.

FIG. 2 is a graph illustrating characteristics of the sensor according to the first embodiment.

The horizontal axis in FIG. 2 is a concentration parameter CP1. The concentration parameter CP1 is the ½ power of the concentration of the detection target gas. An increase in the concentration parameter CP1 corresponds to an increase in the concentration of the detection target gas. The vertical axis is the change $\Delta C$ in the electrical capacitance. The change $\Delta C$ is based on the electrical capacitance when the concentration of the detection target gas is zero. A negative change $\Delta C$ corresponds to a decrease in the electrical capacitance.

As shown in FIG. 2, when the concentration parameter CP1 increases, the change $\Delta C$ in the electrical capacitance is negative and the absolute value of the change $\Delta C$ increases. That is, when the concentration of the detection target gas increases, the electrical capacitance decreases.

As shown in FIG. 2, the concentration of the detection target gas in a first state ST1 (high concentration) is higher than the concentration of the detection target gas in a second state ST2 (low concentration). A first electrical capacitance between the fixed electrode 55 and the movable portion 30M in the first state ST1 is smaller than a second electrical capacitance between the fixed electrode 55 and the movable portion 30M in the second state ST2.

Thus, the change in electrical capacitance corresponds to the concentration of the detection target gas. The detection target gas can be detected by detecting a change in electrical capacitance. For example, the detection target gas can be detected with a high sensitivity of about 1 ppm to 10 ppm.

As shown in FIG. 1, the sensor 110 may further include a controller 70. The controller 70 is configured to detect the electrical capacitance (e.g., first electrical capacitance, second electrical capacitance, etc.).

The change in the electrical capacitance corresponds to the change in the distance dz between the fixed electrode 55 and the movable portion 30M (movable electrode 35). For example, a first distance between the fixed electrode 55 and the movable portion 30 M in the first state ST1 (high concentration) is longer than a second distance between the fixed electrode 55 and the movable portion 30M in the second state ST2 (low concentration).

For example, the change in the distance dz may be detected. For example, the displacement of the movable portion 30M may be detected by an optical method or the like.

As described above, the change in the distance dz may be based on the stress resulting from changes in the volume of first layer 31. For example, a first volume of the first layer 31 in the first state ST1 (high concentration) is smaller than a second volume of the first layer 31 in the second state ST2 (low concentration).

As shown in FIG. 1, the first support layer 31L is provided between the base 40 and the first layer 31 in this example. A second gap G2 is provided between the base 40 and the first 10 support layer 31L.

In this example, the sensor 110 further includes a first connecting portion 31c. A part of the first connecting portion 31c is connected to the first support portion 31s. Another part of the first connecting portion 31c is connected to the movable portion 30M. A third gap G3 is provided between the base 40 and the first connecting portion 31c. For example, the first connecting portion 31c may have a meandering structure.

As shown in FIG. 1, the sensor 110 may include a second fixed portion 22 and a second support portion 32s. The base 40 further includes a third region 43. The first region 41 is between the second region 42 and the third region 43. The second fixed portion 22 is fixed to the third region 43. The second support portion 32s is connected to the second fixed portion 22. The second support portion 32s includes a second support layer 32L and a second layer 32. The second layer 32 is fixed to the second support layer 32L.

The second layer 32 includes oxygen and at least one metal selected from the group consisting of Pt, Pd and Ti. The second layer 32 includes, for example, oxides of the above metals. The second layer 32 includes, for example, bonds of the above metal and oxygen.

The movable portion 30M is provided between the first support portion 31s and the second support portion 32s. The movable portion 30M is supported by the first support portion 31s and the second support portion 32s. A fourth gap G4 is provided between the base 40 and the second support portion 32s. A double-beam structure may be applied.

In this example, the sensor 110 further includes a second connecting portion 32c. A part of the second connecting portion 32c is connected to the second support portion 32s. Another part of the second connecting portion 32c is connected to the movable portion 30M. A fifth gap G5 is provided between the base 40 and the second connecting portion 32c. The second connecting portion 32c has, for example, a meandering structure.

As shown in FIG. 1, the first support portion 31s may include a first conductive member 31h. The second support portion 32s may include a second conductive member 32h. For example, current flowing through the first conductive member 31h can raise the temperature of the first support portion 31s. For example, current flowing through the second conductive member 32h can raise the temperature of the second support portion 32s. For example, by heating the support portions, various substances (including, for example, hydrogen) adsorbed on the first layer 31 and the second layer 32 are released.

As shown in FIG. 1, the first layer 31 includes a first face F1 and a first portion P1. The first portion P1 is provided between the first support layer 31L and the first face F1. The first portion P1 is the center of the first layer 31 in a first direction D1 from the first support layer 31L to the first face F1. The first direction D1 is, for example, a Z-axis direction. One direction perpendicular to the Z-axis direction is defined as an X-axis direction. A direction perpendicular to the Z-axis direction and the X-axis direction is defined as a Y-axis direction. The direction from the first support portion 31s to the movable portion 30M is, for example, the X-axis direction.

A ratio of an absolute value of a difference between a first portion concentration of oxygen in the first portion P1 and a first face concentration of oxygen in the first face F1 to the first portion concentration is not less than 0.1 and not more than 10. The concentration of oxygen is relatively uniform in the thickness direction of the first layer 31.

A thickness of the first layer 31 is, for example, not less than 1 nm and not more than 1 μm. A thickness of the first support layer 31L is, for example, not less than 10 nm and not more than 10 μm. The first support layer 31L includes, for example, silicon oxide.

Some examples of methods for manufacturing the sensor 110 are described below.

Figure 3A:
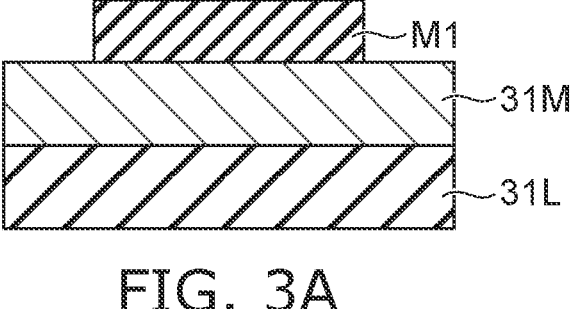
FIGS. 3A to 3C are schematic cross-sectional views illustrating a method for manufacturing the sensor according to the first embodiment.
Figure 3B:
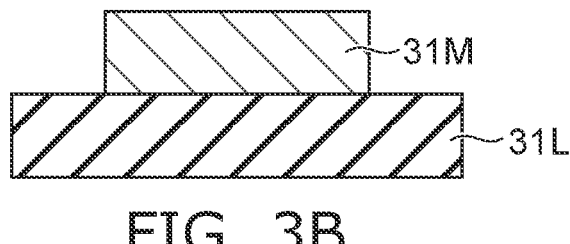
Figure 3C:
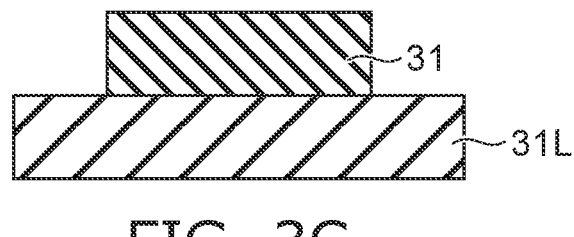

FIGS. 3A to 3C are schematic cross-sectional views illustrating a method for manufacturing the sensor according to the first embodiment.

As shown in FIG. 3A, a first metal film 31M serving as the first layer 31 is provided on the first support layer 31L. The first metal film 31M includes at least one metal selected from the group consisting of Pt, Pd and Ti. A mask M1 (for example, a resist layer) is formed on the first metal film 31M.

As shown in FIG. 3B, using the mask M1 as a mask, the first metal film 31M is processed. In the processing, dry etching or wet etching is performed. After that, the mask M1 is removed.

As shown in FIG. 3C, the first metal film 31M is oxidized by heat-treating the first metal film 31M in an oxygen atmosphere. The first layer 31 is obtained from the first metal film 31M.

Figure 4A:
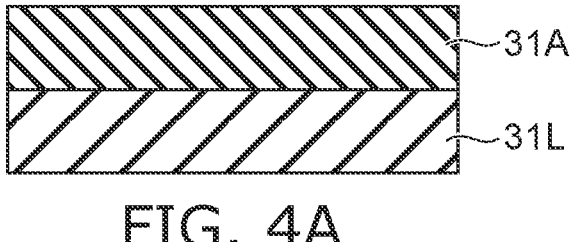
FIGS. 4A to 4C are schematic cross-sectional views illustrating the method for manufacturing the sensor according to the first embodiment.
Figure 4B:
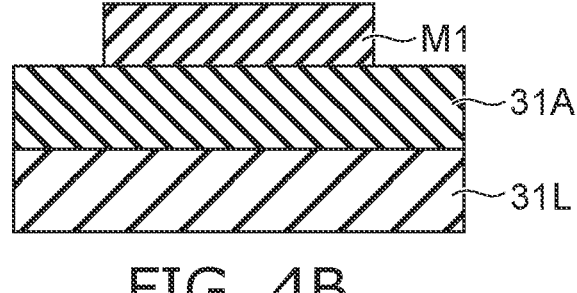
Figure 4C:
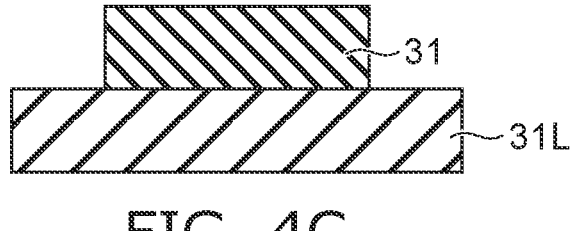

FIGS. 4A to 4C are schematic cross-sectional views illustrating the method for manufacturing the sensor according to the first embodiment.

As shown in FIG. 4A, a metal film is formed on the first support layer 31L in an atmosphere including oxygen. Thereby, the metal oxide layer 31A is obtained. As shown in FIG. 4B, a mask M1 is formed on the metal oxide layer 31A. As shown in FIG. 4C, the first layer 31 is obtained by processing the metal oxide layer 31A using the mask M1 as a mask.

5

Figure 5A:
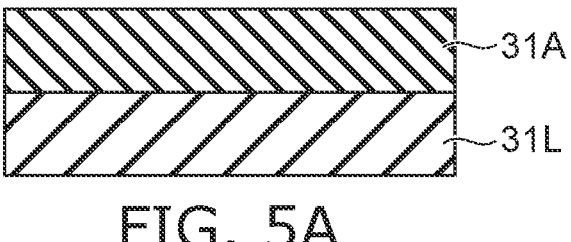
FIGS. 5A to 5C are schematic cross-sectional views illustrating the method for manufacturing the sensor according to the first embodiment.
Figure 5B:
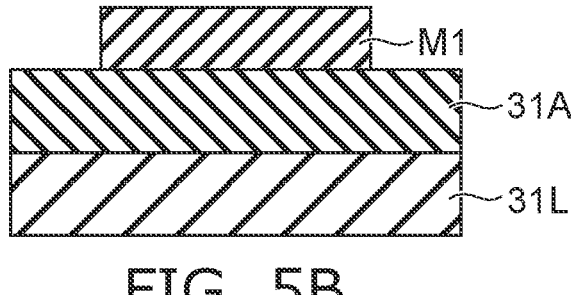
Figure 5C:
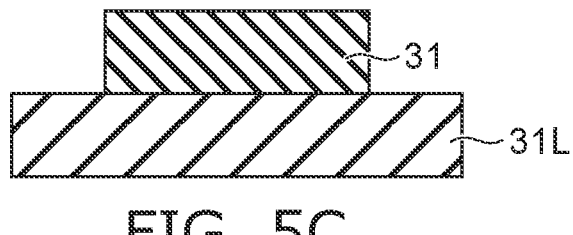

FIGS. 5A to 5C are schematic cross-sectional views illustrating the method for manufacturing the sensor according to the first embodiment.

As shown in FIG. 5A, the metal oxide layer 31A is formed on the first support layer 31L by using a target including metal oxide. As shown in FIG. 5B, a mask M1 is formed on the metal oxide layer 31A. As shown in FIG. 5C, the first layer 31 is obtained by processing the metal oxide layer 31A using the mask M1 as a mask.

The detection target gas is hydrogen, for example. Hydrogen, for example, is produced from various resources. The various resources include, for example, fossil fuels, by-product gases from factories, biomass, or natural energy. Hydrogen attracts attention as a clean energy. Since hydrogen is a combustible gas, it is desirable to detect hydrogen with high sensitivity. For example, a high-speed, low-power hydrogen sensor is required.

For example, hydrogen is produced at the same time as carbon monoxide in incomplete combustion. An initial fire can be detected by detecting hydrogen. For example, the intestinal environment can be predicted by measuring hydrogen gas in breath. For example, highly sensitive detection of hydrogen could facilitate healthcare. In various applications such as those mentioned above, the concentration of hydrogen is low. For example, it is desired to detect hydrogen at a low concentration of about 1 ppm.

There are resistance change type and semiconductor type hydrogen sensors. There is a limit to decrease the power consumption in these hydrogen sensors.

In the embodiment, for example, the first layer 31 is reduced by the detection target gas (hydrogen). As a result, the first support portion 31s including the first layer 31 is deformed. The deformation of the first support portion 31s is detected, for example, as a change in electrical capacitance.

In the embodiments, the first layer 31 (sensitive film) includes a metal oxide. The metal oxides have catalytic activity. When a reducing gas such as hydrogen approaches the sensitive film, the film stress changes in the tensile stress direction. The concentration of oxygen in the sensitive film changes depending on the concentration (including the presence or absence) of the detection target gas.

For example, when a reducing gas such as hydrogen approaches the sensitive film, hydrogen molecules are dissociated into hydrogen atoms on the sensitive film surface. The hydrogen atoms reduce the metal oxide, forming water and leaving. The frequency of this reaction depends on the hydrogen concentration. When the amount of oxygen in the sensitive film decreases, the film stress changes in the tensile direction.

In the embodiments, for example, catalytic metal oxide reduction is utilized. For example, metal oxides are reduced by the reducing the detection target gas. This changes the volume of the layer including the catalyst metal. The change in the volume is detected as a change in electrical capacitance. By utilizing the reducing action, it is possible to detect the concentration of a very small amount of reducing gas of about 1 ppm with high sensitivity.

The embodiments may include the following configurations (for example, technical proposals).

Configuration 1

A sensor, comprising:
a base including a first region and a second region;
a fixed electrode fixed to the first region;
a first fixed portion fixed to the second region;

a first support portion connected to the first fixed portion, the first support portion including a first support layer and a first layer fixed to the first support layer, the first layer including at least one metal selected from the group consisting of Pt, Pd and Ti, and oxygen; and
a movable portion supported by the first support portion, a first gap being provided between the fixed electrode and the movable portion.

Configuration 2

The sensor according to Configuration 1, wherein
the first layer is configured to be reduced by a detection target gas around the first layer.

Configuration 3

The sensor according to Configuration 2, wherein
the detection target gas includes hydrogen.

Configuration 4

The sensor according to Configuration 1, wherein
a concentration of the detection target gas in a first state is higher than a concentration of the detection target gas in a second state, and
a first distance between the fixed electrode and the movable portion in the first state is longer than a second distance between the fixed electrode and the movable portion in the second state.

Configuration 5

The sensor according to Configuration 1, wherein
a concentration of the detection target gas in a first state is higher than a concentration of the detection target gas in a second state, and
a first volume of the first layer in the first state is smaller than a second volume of the first layer in the second state.

Configuration 6

The sensor according to Configuration 1, wherein
a concentration of the detection target gas in a first state is higher than a concentration of the detection target gas in a second state, and
a first electrical capacitance between the fixed electrode and the movable portion in the first state is smaller than a second electrical capacitance between the fixed electrode and the movable portion in the second state.

Configuration 7

The sensor according to Configuration 6, further comprising:
a controller configured to detect the first electrical capacitance and the second electrical capacitance.

Configuration 8

The sensor according to any one of Configurations 1-7, wherein
the first layer includes an oxide of the metal.

Configuration 9

The sensor according to any one of Configurations 1-7, wherein the first layer includes a bond between the metal and oxygen.

Configuration 10

The sensor according to any one of Configurations 1-9, wherein the first layer includes a first face and a first portion, the first portion is between the first support layer and the first face, the first portion is a center of the first layer in a first direction from the first support layer to the first face, and a ratio of an absolute value of a difference between a first portion concentration of oxygen in the first portion and a first face concentration of oxygen in the first face to the first partial concentration is not less than 0.1 and not more than 10.

Configuration 11

The sensor according to any one of Configurations 1-10, wherein a thickness of the first layer is not less than 1 nm and not more than 1 μm.

Configuration 12

The sensor according to Configuration 11, wherein a thickness of the first support layer is not less than 10 nm and not more than 10 μm.

Configuration 13

The sensor according to any one of Configurations 1-12, wherein the first support portion further includes a first conductive member, and a temperature of the first support portion can be increased by a current flowing through the first conductive member.

Configuration 14

The sensor according to any one of Configurations 1-13, wherein the first support layer includes silicon oxide.

Configuration 15

The sensor according to any one of Configurations 1-14, wherein the first support layer is provided between the base and the first layer, and a second gap is provided between the base and the first support layer.

Configuration 16

The sensor according to Configuration 15, further comprising:

a first connecting portion, a part of the first connecting portion being connected to the first support portion, another part of the first connecting portion being connected to the movable portion, and a third gap being provided between the base and the first connecting portion.

Configuration 17

The sensor according to Configuration 16, wherein the first connecting portion has a meandering structure.

Configuration 18

The sensor according to any one of Configurations 1-17, further comprising:

a second fixed portion; and a second support portion, the base further including a third region, the first region being between the second region and the third region, the second fixed portion being fixed to the third region, the second support portion being connected to the second fixed portion, the second support portion including a second support layer and a second layer fixed to the second support layer, the second layer including at least one metal selected from the group consisting of Pt, Pd and Ti, and oxygen, and the movable portion being provided between the first support portion and the second support portion and being further supported by the second support portion.

Configuration 19

The sensor according to Configuration 18, further comprising:

a second connecting portion, a part of the second connecting portion being connected to the second support portion, another part of the second connecting portion being connected to the movable portion, and a gap being provided between the base and the second connecting portion.

Configuration 20

The sensor according to Configuration 19, wherein the second connecting portion has a meandering structure.

According to the embodiments, it is possible to provide a sensor with high detection sensitivity.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as, bases, fixed portions, support portions, movable portions, fixed electrodes, controllers, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a base including a first region and a second region;
a fixed electrode fixed to the first region;
a first fixed portion fixed to the second region;
a first support portion connected to the first fixed portion, the first support portion including a first support layer and a first layer fixed to the first support layer, the first layer including at least one metal selected from the group consisting of Pt, Pd and Ti, and oxygen; and
a movable portion supported by the first support portion, a first gap being provided between the fixed electrode and the movable portion,
wherein
the first layer includes a first face and a first portion,
the first portion is between the first support layer and the first face,
the first portion is a center of the first layer in a first direction from the first support layer to the first face, and
a ratio of an absolute value of a difference between a first portion concentration of oxygen in the first portion and a first face concentration of oxygen in the first face to the first portion concentration is not less than 0.1 and not more than 10.

2. The sensor according to claim 1, wherein
the first layer is configured to be reduced by a detection target gas around the first layer.

3. The sensor according to claim 2, wherein
the detection target gas includes hydrogen.

4. The sensor according to claim 1, wherein
a concentration of a detection target gas in a first state is higher than a concentration of the detection target gas in a second state, and
a first distance between the fixed electrode and the movable portion in the first state is longer than a second distance between the fixed electrode and the movable portion in the second state.

5. The sensor according to claim 1, wherein
a concentration of the detection target gas in a first state is higher than a concentration of the detection target gas in a second state, and
a first volume of the first layer in the first state is smaller than a second volume of the first layer in the second state.

6. The sensor according to claim 1, wherein
a concentration of the detection target gas in a first state is higher than a concentration of the detection target gas in a second state, and
a first electrical capacitance between the fixed electrode and the movable portion in the first state is smaller than a second electrical capacitance between the fixed electrode and the movable portion in the second state.

7. The sensor according to claim 6, further comprising:
a controller configured to detect the first electrical capacitance and the second electrical capacitance.

8. The sensor according to claim 1, wherein
the first layer includes an oxide of the metal.

9. The sensor according to claim 1, wherein
the first layer includes a bond between the metal and oxygen.

10. The sensor according to claim 1, wherein
a thickness of the first layer is not less than 1 nm and not more than 1 μm.

11. The sensor according to claim 10, wherein
a thickness of the first support layer is not less than 10 nm and not more than 10 μm.

12. The sensor according to claim 1, wherein
the first support portion further includes a first conductive member, and
a temperature of the first support portion can be increased by a current flowing through the first conductive member.

13. The sensor according to claim 1, wherein
the first support layer includes silicon oxide.

14. The sensor according to claim 1, wherein
the first support layer is provided between the base and the first layer, and
a second gap is provided between the base and the first support layer.

15. The sensor according to claim 14, further comprising:
a first connecting portion,
a part of the first connecting portion being connected to the first support portion,
another part of the first connecting portion being connected to the movable portion, and
a third gap being provided between the base and the first connecting portion.

16. The sensor according to claim 15, wherein
the first connecting portion has a meandering structure.

17. The sensor according to claim 1, further comprising:
a second fixed portion; and
a second support portion,
the base further including a third region,
the first region being between the second region and the third region,
the second fixed portion being fixed to the third region,
the second support portion being connected to the second fixed portion,
the second support portion including a second support layer and a second layer fixed to the second support layer, the second layer including at least one metal selected from the group consisting of Pt, Pd and Ti, and oxygen, and the movable portion being provided between the first support portion and the second support portion and being further supported by the second support portion.

18. The sensor according to claim 17, further comprising:

a second connecting portion, a part of the second connecting portion being connected to the second support portion, another part of the second connecting portion being connected to the movable portion, and a gap being provided between the base and the second connecting portion.

19. The sensor according to claim 18, wherein the second connecting portion has a meandering structure.

\* \* \* \* \*